(12) United States Patent
Grodzins

(10) Patent No.: US 8,494,113 B2
(45) Date of Patent: Jul. 23, 2013

(54) AUTOMATED SUM-PEAK SUPPRESSION IN AN X-RAY FLUORESCENCE ANALYZER

(75) Inventor: Lee Grodzins, Lexington, MA (US)

(73) Assignee: Thermo Scientific Portable Analytical Instruments Inc., Tewksbury, MA (US)

( * ) Notice: Subject to any disclaimer, the term of this patent is extended or adjusted under 35 U.S.C. 154(b) by 416 days.

(21) Appl. No.: 12/636,453

(22) Filed: Dec. 11, 2009

(65) Prior Publication Data
US 2010/0150307 A1      Jun. 17, 2010

Related U.S. Application Data

(60) Provisional application No. 61/122,026, filed on Dec. 12, 2008.

(51) Int. Cl.
*G01N 23/223* (2006.01)
(52) U.S. Cl.
USPC .............................................. 378/45; 378/44
(58) Field of Classification Search
USPC ........................................ 378/44, 45, 48, 50
See application file for complete search history.

(56) References Cited

U.S. PATENT DOCUMENTS

| | | |
|---|---|---|
| 4,686,694 A | 8/1987 | Berry et al. |
| 5,422,925 A | 6/1995 | Komatsu et al. |
| 5,430,786 A | 7/1995 | Komatsu et al. |
| 5,497,407 A | 3/1996 | Komatsu et al. |
| 6,968,043 B2 | 11/2005 | Amemiya et al. |
| 2004/0109534 A1 | 6/2004 | Uehara et al. |
| 2004/0136500 A1 | 7/2004 | Amemiya et al. |
| 2005/0139776 A1 | 6/2005 | Reiter |
| 2006/0193433 A1 | 8/2006 | Ledoux et al. |
| 2008/0205592 A1 | 8/2008 | Conners et al. |
| 2008/0319714 A1 | 12/2008 | Camus et al. |
| 2009/0032715 A1 | 2/2009 | Mott |
| 2009/0034682 A1 | 2/2009 | Mott |
| 2009/0037126 A1 | 2/2009 | Mott |

FOREIGN PATENT DOCUMENTS

| | | |
|---|---|---|
| EP | 1 840 561 A2 | 10/2007 |
| JP | 2006-38822 | 2/2006 |
| WO | WO 2008/157734 A2 | 12/2008 |
| WO | WO 2009/020863 A1 | 2/2009 |
| WO | WO 2009/020866 A1 | 2/2009 |
| WO | WO 2009/032452 A1 | 3/2009 |

OTHER PUBLICATIONS

Translation of JP 2006-038822 published in 2006.*

(Continued)

*Primary Examiner* — Glen Kao
(74) *Attorney, Agent, or Firm* — Gordon Stewart

(57) ABSTRACT

A method of operating an x-ray fluorescence (XRF) analyzer to automatically suppress sum-peaks is disclosed. The method includes irradiating a sample to acquire an initial energy spectrum. The energy spectrum is processed to identify a sum-peak that interferes with a characteristic fluoresced peak of an element of interest. A filter is positioned in the emitted radiation path to attenuate radiation that contributes to the identified sum-peak, and a filtered energy spectrum is acquired. In certain embodiments, the filtered energy spectrum is acquired only when a limit of detection (LOD) of an element of interest calculated from the initial energy spectrum does not satisfy a targeted objective.

16 Claims, 5 Drawing Sheets

OTHER PUBLICATIONS

Amptec Inc., "Quantitative Analysis Software for X-ray Fluorescence: Use with the MCA8000A Multichannel Analyzer," (2004), http://www.fastcomtec.com/fwww/datashee/det/xrffp.pdf, pp. 1-4.

Marumo et al., "Determination of Arsenic and Lead Concentrations in Soil Using Energy-Dispersive X-Ray Fluorescence Spectrometry," (2005), http://sciencelinks.jp/j-east/article/200509/000020050905A0362765.php, pp. 1-2.

Marumo et al., "Determination of Arsenic and Lead Concentrations in Soil Using Energy-Dispersive X-Ray Fluorescence Spectrometry," Adv. X-Ray chem. Anal., Japan 36, pp. 17-36 (2005).

* cited by examiner

AUTOMATED SUM-PEAK SUPPRESSION IN AN X-RAY FLUORESCENCE ANALYZER

CROSS-REFERENCE TO RELATED APPLICATION

This application claims the priority benefit under 35 U.S.C. §119(e) of U.S. provisional application No. 61/122,026 entitled "Automated Sum-Peak Suppression", filed on Dec. 12, 2008, the entire disclosure of which is incorporated herein by reference.

FIELD OF THE INVENTION

The present invention relates generally to the measurement of elemental composition by x-ray fluorescence, and more particularly to method and device for identifying and suppressing interfering sum-peaks in a detected energy spectrum.

BACKGROUND OF THE INVENTION

Energy dispersive x-ray fluorescence (XRF) is a well-established technique for the measurement of elemental composition of a variety of materials. In XRF analysis, a beam of radiation is directed onto the sample to produce fluorescent emission of characteristic x-rays. The emitted x-rays are received by a detector, which responsively generates signal pulses representative of the energies of the detected x-rays. A programmable processor accumulates and analyzes the detector pulse signals to construct a plot of x-ray count rate versus energy, referred to as an energy spectrum. The energy spectrum will typically include one or more characteristic peaks corresponding to fluorescent emission by atoms of an element of interest, together with scattered radiation peaks and artifact peaks arising from various noise sources.

One type of artifact peak is known as a sum-peak, which is caused by the simultaneous or near-simultaneous reception by the detector of two or more x-rays. The processor interprets the resultant pulse as a single x-ray having an energy equal to the combined energies of the two or more individual x-rays. The presence of a sum-peak in the energy spectrum may compromise instrument performance in a situation where the sum-peak interferes with (i.e., overlaps) a characteristic peak of an element of interest. Accurate quantification of the element's concentration in the sample based on the intensity of the composite (overlapped) peak requires that the contribution of the sum-peak be accounted for. While algorithms are known in the XRF art for estimating sum-peak count rates, the use of such algorithms introduce uncertainties that increases the instrument's limit of detection (LOD) of the element of interest and adversely impacts the ability of the instrument to reliably detect the presence of the element of interest when present in low concentrations. Uncertainty arising from interfering sum-peaks in the energy spectrum is particularly problematic in view of the trend toward more stringent regulation of lead and other hazardous substances in consumer products, which imposes a need to detect the hazardous substance at progressively smaller LODs.

SUMMARY

Roughly described, a method is provided for operating an XRF analyzer that includes steps for automatically identifying and suppressing a sum-peak that interferes with (i.e., overlaps) a characteristic peak of an element of interest, thereby ensuring that the limit of detection (LOD) of the element meets a targeted objective. A sample to be analyzed is irradiated with a primary x-ray beam, and atoms within the sample responsively emit fluoresced radiation of characteristic energies. At least a portion of the fluoresced radiation is received by a detector, which generates signal pulses representative of the intensities and energies of the detected radiation. The signal pulses are accumulated and analyzed by a processor to construct an initial energy spectrum, which will include at least one characteristic peak corresponding to the fluorescent emission from an element of interest in the sample. The energy spectrum is processed to identify whether the characteristic peak overlaps with a sum-peak. If an interfering sum-peak is identified, a filter is automatically positioned in the emitted radiation path. The filter is constructed from a material or combination of materials that inhibits the transmission of radiation of energies that contribute to the formation of the identified sum-peak, but transmits the characteristic peak with relatively little attenuation. As shown by example below, this is readily achieved since the energy of the characteristic peak is always considerably higher than the energy(ies) of at least one of the summing peaks. The filtered radiation is received by a detector, and the responsively generated pulses are accumulated and analyzed to generate a filtered energy spectrum in which the interfering sum-peak is suppressed, thereby lowering the limit of detection (LOD) of the element of interest.

In accordance with a more specific aspect of the invention, an LOD of the element of interest is determined from the initial energy spectrum, taking into account the uncertainty arising from subtraction of the contribution of the interfering sum-peak, and the filtering/filtered energy spectrum acquisition steps may be performed only if the determined LOD does not meet a targeted objective.

According to another specific aspect the intensity or other characteristics of the x-ray beam are adjusted during the acquisition of the filtered spectrum to compensate for attenuation of the fluoresced radiation of the element of interest by the filter.

In accordance with yet another aspect of the invention, the filter is selected from a plurality of available filters of different properties (e.g., composition and/or thickness) depending on the energy(ies) of the radiation giving rise to the interfering sum-peak.

An XRF analyzer that embodies the foregoing method may include an x-ray tube or radioisotope source for producing the primary x-ray beam, a silicon drift diode (SDD) or equivalent detector for detecting the emitted radiation, and a movable filter apparatus having at least one filter mounted thereon for positioning a selected filter in the emitted radiation path. The XRF analyzer may be further equipped with a programmable controller programmed with instructions for identifying the sum-peak that interferes with a characteristic peak of an element of interest, for determining an LOD of the element of interest in view of the presence of the sum-peak, and for causing a selected filter to be positioned in the emitted radiation path if the determined LOD does not meet a targeted objective. The controller may additionally be programmed with instructions for adjusting x-ray source operating parameters (e.g., x-ray tube current) to compensate for attenuation of the fluoresced radiation of the element of interest by the filter. In one preferred implementation, the x-ray source, detector, filter apparatus and controller are commonly housed within a structure designed to be handheld by an operator.

DETAILED DESCRIPTION OF EMBODIMENTS

Preferred embodiments of the invention are described below in connection with the FIG. 1 XRF analyzer and the methods depicted in the FIGS. 2 and 3 flowcharts. It will be understood that the embodiments and examples discussed below are intended to illustrate rather than to limit the invention.

Figure 1:
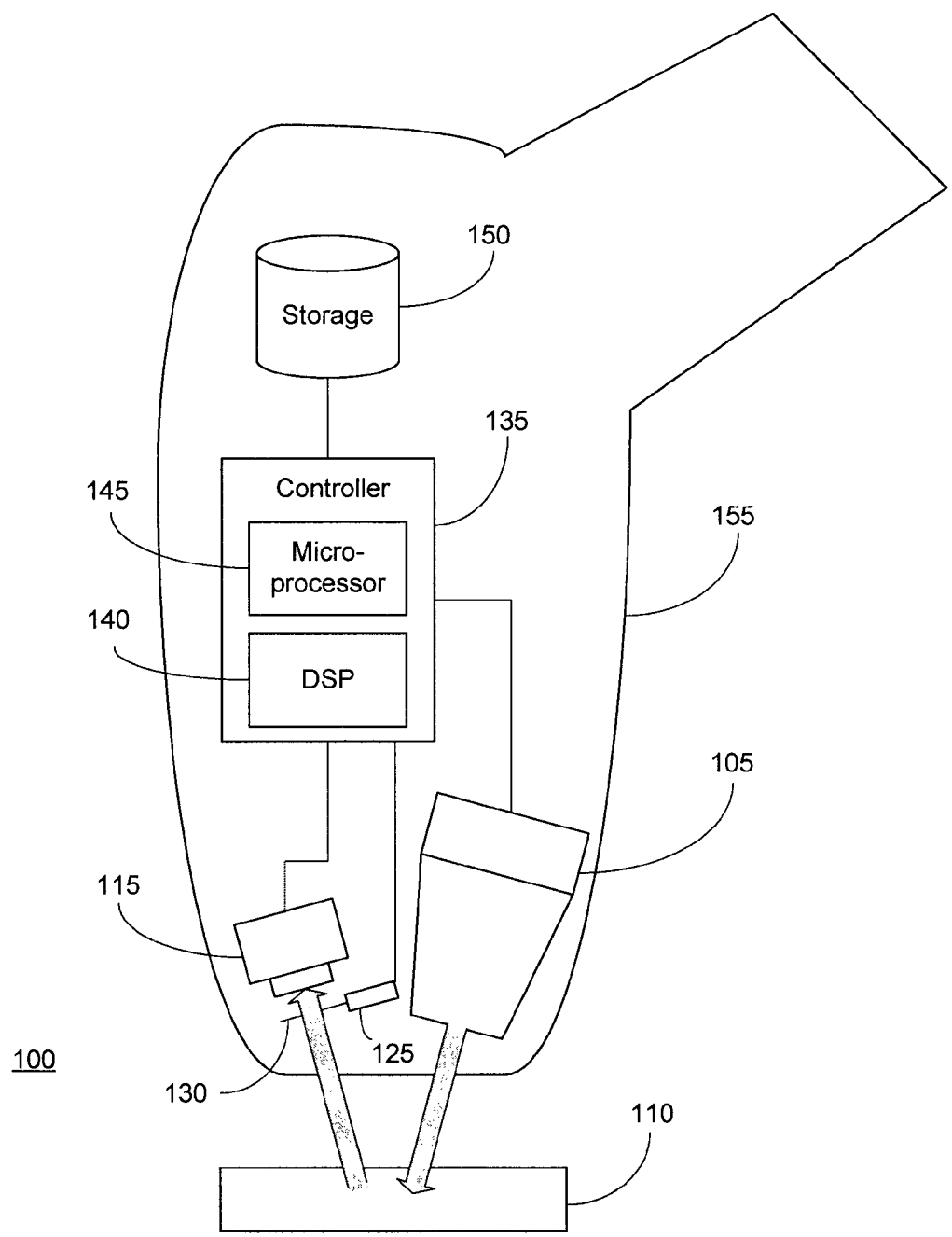
FIG. 1 is a symbolic diagram of an XRF analyzer.

FIG. 1 is a symbolic diagram of the components of an XRF analyzer 100 in which the automated sum-peak suppression techniques of the present invention may be advantageously implemented. XRF analyzer 100 includes an x-ray source 105 for generating a primary radiation beam to excite atoms in sample 110. X-ray source 105 may take the form of any suitable x-ray tube or radioisotope source. As used herein, the term "x-ray" is broadly defined to include any radiation having an energy suitable for causing fluorescence of the element (s) of interest via ejection of an inner shell electron, and may encompass radiation classified as gamma-rays in other contexts. One or more not-depicted structures, such as filters, concentrators and collimators, may be positioned in the primary x-ray beam to tailor the energetic and/or geometric parameters of the x-ray beam so as to optimize the analyzer performance for specific applications.

Detector 115 is positioned to receive radiation emitted by sample 110. The emitted radiation will typically comprise a mixture of fluorescent x-rays characteristic of specific elements in sample 110 and elastically scattered (Rayleigh) and inelastically scattered (Compton) x-rays. The design and operation of XRF detectors are well known in the art and hence will not be discussed herein. Generally described, detector 115 generates a signal pulse in response to reception of an x-ray photon, the size of the pulse being representative of the photon's energy. Detector 115 may incorporate or have associated therewith preamplifier circuitry for integrating and amplifying current produced by the detector 115 crystal. In various implementations, detector 115 may take the form of a silicon PIN detector, cadmium telluride detector, or silicon drift detector.

A filter apparatus 125 is operable to selectively position a filter 130 in the path of the radiation emitted by sample 110, such that x-rays of undesirable energies are preferentially absorbed or otherwise attenuated before the radiation reaches detector 115. The operation of filter apparatus 125 will be discussed below in connection with FIG. 2. Filter apparatus 125 may include a single filter that is controllably moveable between a first position that intersects the emitted radiation path, and a second position in which the filter is located outside of the emitted radiation path. In an alternative implementation, filter apparatus 125 includes a rotatable filter wheel having two or more filters of differing compositions and/or thicknesses.

The output of detector 115 is conveyed to programmable controller 135, which will typically incorporate at least one digital signal processor (DSP) 140 programmed to amplify, process and accumulate the signal pulses such that an energy spectrum of the detected radiation may be constructed. As is known in the art, DSP 140 may execute pulse pileup rejection routines for rejecting nearly coincident pulses generated by detector 115; however, such routines have limited efficiency, particularly at low detected x-ray energies where the amplitude of the detected events approaches that of noise events. Programmable controller 135 may also include a specialized or general purpose microprocessor 145 for executing program instructions relating to data acquisition and analysis and instrument control, including implementations of the method steps depicted in FIGS. 2 and 3 and discussed below. The program instructions executed by DSP 140 and microprocessor 145 may be stored in hardware, firmware or software form within controller 135 and/or non-volatile storage 150 coupled to controller 125. Storage 150 may also hold test results and information input by the operator.

The various components of XRF analyzer 100 may be located within a common housing 155 designed to be handheld by the operator. A touch screen display (not depicted) may be incorporated into or mounted to housing 155 to present text and graphics (e.g., representing analysis results) and to accept operator input. XRF analyzer 100 will typically include a wired (e.g., USB) or wireless (e.g., 802.11g) communications port to enable the uploading and downloading of analysis results, software, and other information to and form an external computer. In alternative implementations, certain of the components of XRF analyzer 100 may be located remotely from each other, e.g., components of controller 135 may reside on a general purpose computer that communicates with the other components over a wired or wireless connection.

Figure 2:
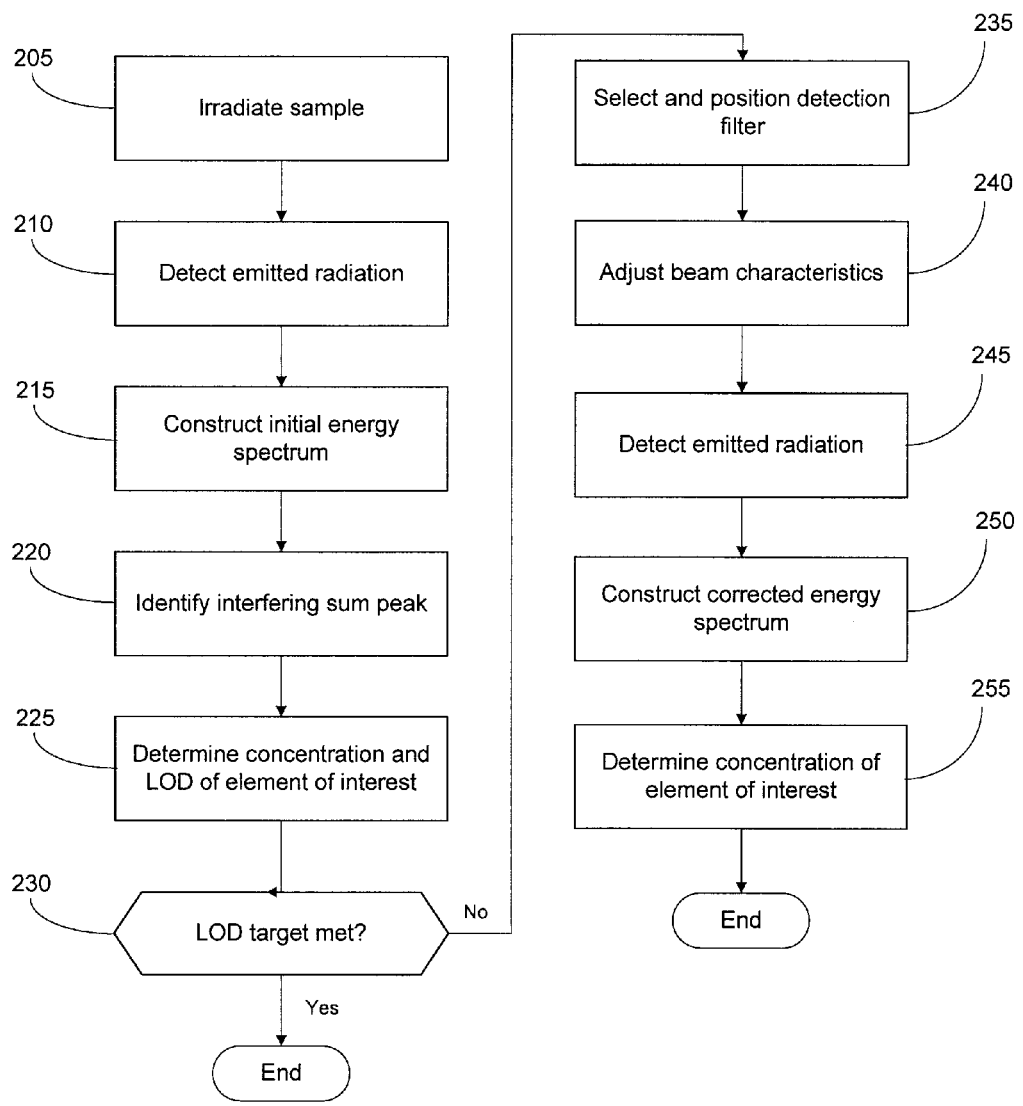
FIG. 2 is a flowchart depicting steps of a method of operating an XRF analyzer, in accordance with an illustrative embodiment of the invention.
Figure 3:
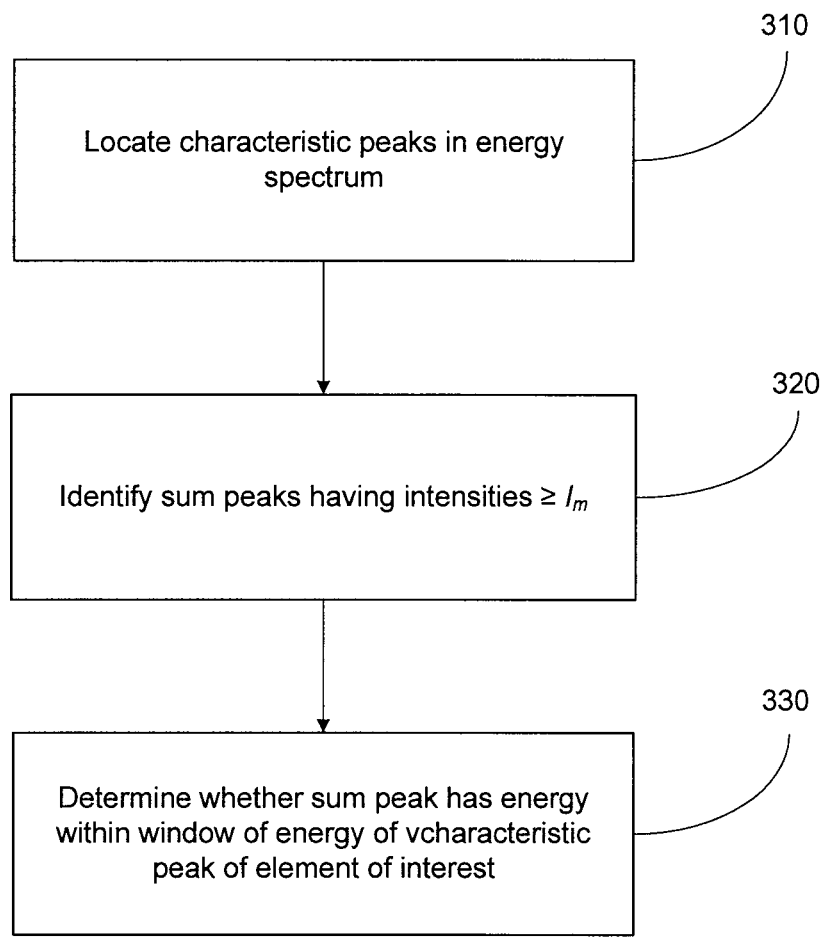
FIG. 3 is a flowchart depicting steps of a specific method for identifying the presence of interfering sum-peaks in an energy spectrum.

FIG. 2 shows the steps of a method for operating an XRF instrument to automatically identify interfering sum-peaks in acquired energy spectra and to suppress the identified sum-peaks such that the concentration of one or more elements in sample 110 may be measured at targeted LODs. It should be noted that although the steps are presented in a particular order in the flowchart, certain of the steps will typically be conducted concurrently rather than sequentially, and so the flowchart should not be regarding as imposing a fixed sequence.

In step 205, a beam of primary x-ray radiation is directed unto the sample, e.g., by operation of x-ray source 105. This step may be initiated by operator action, such as be depressing a trigger mounted to housing 155. The operation of x-ray source 105 is preferably directed by controller 135, and certain of the beam parameters, such as intensity, energy and geometry, may be selected or adjusted based on operator input, for example by specifying the class or type of material. Alternatively, the beam characteristics may be automatically optimized for a particular application based on information acquired early in an analysis cycle. For example, the initial energy spectrum acquired in step 210 may indicate the presence of elements commonly present in a particular type of plastic, and the beam characteristics may be adjusted accordingly to optimize compositional analysis for that plastic type.

A portion of the radiation emitted by sample 110, including fluoresced and scattered radiation, is received by detector 115 in step 210. During this step, filter apparatus 125 is operated (by direction of controller 135) to provide no or minimal filtration of the emitted radiation, e.g., by moving filter 130 away from the emitted beam path. As discussed above, detector 115 produces a series of pulses responsive to the reception of radiation, with each pulse being representative of the energy of a detected x-ray. The exact or near coincidence of two or more x-rays on detector 115 may produce a pulse that appears to arise from detection of a single x-ray having an energy equal to the combined energies of the coincident x-rays, and thereby produces a sum-peak in the resultant energy spectrum.

Figure 4:
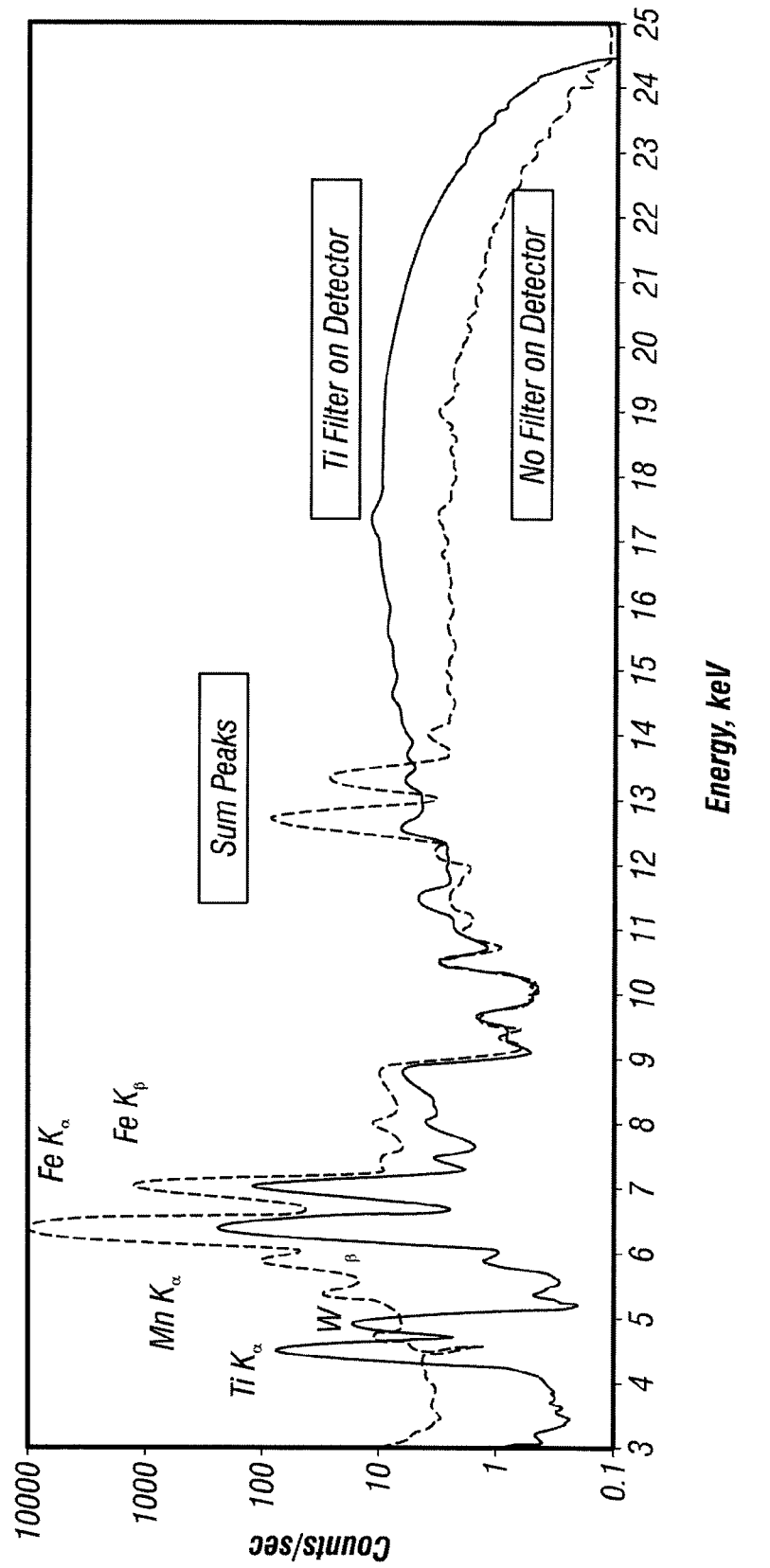
FIG. 4 depicts energy spectra of radiation emitted from an alloy sample acquired in unfiltered and filtered modes.

Controller 135 receives pulses generated by detector 115, and DSP 140 processes and accumulates the pulses over an analysis time to construct an initial energy spectrum, step 215. The total analysis time, i.e., the period over which the sample is irradiated and the emitted radiation is detected and processed, may be controlled by the operator, set to a fixed value, or may be adjusted based on evaluation of the energy spectrum as it is acquired (e.g., terminating the analysis when a specified number of counts have been detected, or when a targeted signal-to-noise ratio has been achieved). As noted above, the resultant energy spectrum contains one or more characteristic emission peaks of the element of interest (i.e., the element sought to be measured), characteristic emission peaks of other elements in sample, and peaks corresponding to coherently and incoherently scattered radiation. The dashed line of FIG. 4 represents an initial energy spectrum of an iron alloy having a lead content of 0.093%, acquired by irradiation with a primary x-ray beam produced by an x-ray tube operated at a voltage of 30 keV, and with no filtration of the emitted radiation. The initial energy spectrum includes large peaks corresponding to the characteristic $K_\alpha$ (6.4 keV) and $K_\beta$ (7.0 keV) lines of iron as well as smaller peaks corresponding to the $K_\alpha$ (5.8 keV) line of manganese and the $K_\alpha$ (10.5 keV) line of lead. Also evident in the energy spectrum are relatively large sum-peaks appearing at about 12.8 keV, 13.4 keV and 13.9 keV, which arise from simultaneous or near-simultaneous reception by detector 115 of $K_\alpha$ and $K_\beta$ fluoresced radiation of iron in different combinations (the 12.8 keV peak is attributable to coincidence of two $K_\alpha$ x-rays, the 13.4 keV peak is attributable to coincidence of $K_\alpha$ and $K_\beta$ x-rays, and the 13.9 keV peak is attributable to coincidence of two $K_\beta$ x-rays).

Figure 5:
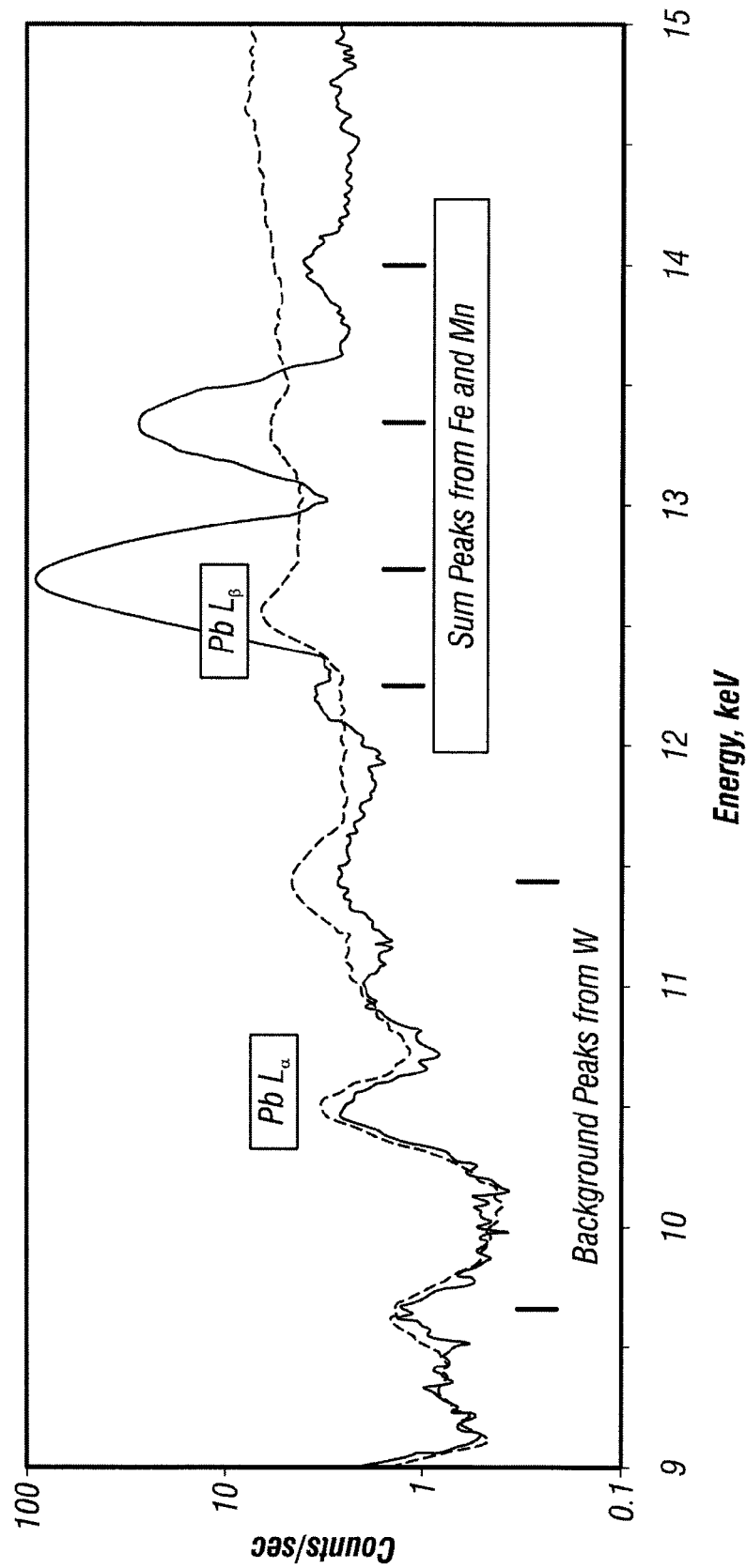
FIG. 5 depicts the region of the energy spectra of FIG. 4 between 9 and 15 keV.

FIG. 5 shows the portion of the spectrum of FIG. 4 over the energy range from 9 keV to 15 keV, a range that encompasses the characteristic L lines of lead at 10.5 keV and 12.6 keV. The solid curve of FIG. 5, obtained without the sum-peak suppression filter, shows an uncontaminated line at 10.5 keV. The 12.6 keV peak, however, is completely obscured, by a factor of about 20, by the sum-peak at 12.8 keV arising from two simultaneous 6.4 keV x-rays. The peak at 10.5 keV, labeled Pb $L_\alpha$, is itself ambiguous and cannot be used for quantitative measurements of Pb unless it is certain that no arsenic exists in the sample. The reason is that the energy of the $K_\alpha$ characteristic line of arsenic is 10.543 keV, which is indistinguishable from the 10.549 keV $L_\alpha$ line of Pb. Both lead and arsenic may be sought-for toxic elements and can be present in ppm concentrations. For an unambiguous measurement of lead, one must use the $L_\beta$ line at 12.6 keV. Without a sum-peak filter, however, the intensity of the $L_\beta$ line at 12.6 keV must be pulled from the huge background of the sum-peak. As will be discussed below, the intensity of the lead $L_\beta$ peak may be determined by subtracting the estimated contribution of the interfering sum-peak; however, this operation will introduce uncertainty and increase the instrument's LOD for lead.

In step 220, the acquired initial energy spectrum is analyzed to ascertain whether any sum-peaks interfere with, i.e., overlap, the characteristic peak(s) of the element of interest. In one specific embodiment, this analysis may be conducted by operation of microprocessor 145 executing instructions embodying the steps depicted in the FIG. 3 flowchart. In step 310, at least a portion of the characteristic peaks in the energy spectrum are located, using known information regarding the characteristic peak energies as well as any a priori knowledge of the elemental composition of sample 110. In certain implementations, only the N most intense characteristic peaks in the spectrum, or those peaks exceeding an intensity threshold, are identified. For example, the method would identify the iron $K_\alpha$ and $K_\beta$ peaks in the FIG. 4 initial energy spectrum, and possibly the smaller $K_\alpha$ manganese peak as well.

Next, in step 320 the method identifies which of the characteristic peaks (other than the characteristic peak of the element of interest) in the spectrum produce sum-peaks that have count rates exceeding a threshold $I_m$. This threshold may be fixed for a particular application and material type, or may be dynamically determined from information in the energy spectrum. It is known that the count rate of a sum-peak $I(E_i + E_j)$ arising from the time overlap of two x-rays of energies $E_i$ and $E_j$ is given by the equation:

$$I(E_i + E_j) = \tau * I(E_i) * I(E_j)$$

where $\tau$ is the time window during which detector 115 and associated circuitry cannot distinguish a single x-ray from multiple coincident x-rays (which has a fixed value for a given detector/processor design) and $I(E_i)$ and $I(E_j)$ are the count rates of the characteristic peaks at $E_i$ and $E_j$, respectively.

Thus, the criterion applied in step 320 is whether, for each sum-peak $I(E_i + E_j)$ produced by coincidence of x-rays of the identified characteristic peaks:

$$I(E_i) * I(E_j) \geq \frac{I_m}{\tau}$$

Typical values for $I_m$ and $\tau$ are 1 count/second and $10^{-7}$, respectively. Step 320 may begin with applying the foregoing criteria to sum-peaks produced by x-rays of the most intense characteristic peak $I(E_1)$, and proceed through x-rays corresponding to peaks having lesser intensities. It will be recognized that the most intense sum-peak will be generated by the simultaneous detection of two x-rays of energy $E_1$, as illustrated by the energy spectrum of FIG. 4, in which the sum-peak appearing at 12.8 keV is produced from the coincidence of two x-rays of energy 6.4 keV (the $K_\alpha$ line of iron, which produces the most intense peak in the spectrum). Step 225 may also include a procedure for determining if any three-fold sum-peaks (sum-peaks produced by co-incidence of three x-rays on detector 115) have intensities that exceed the threshold $I_m$ by applying the following criterion:

$$I(E_i) * I(E_j) * I(E_k) \geq \frac{I_m}{\tau^2}$$

In step 330, for each of the (two-fold or three-fold) sum-peaks that satisfy the criteria set forth above, it is determined whether the sum-peak energy ($E_i + E_j$ or $E_i + E_j + E_k$) is equal to or within a window of the energy of a characteristic peak of the element of interest, i.e., whether the sum-peak overlaps with the characteristic peak and thus interferes with the measurement of the concentration of the element of interest in sample 110. The size of the window may be fixed (either in the form of a stored default value or an operator-specified value) or may be dynamically set based on instrument resolution or other parameters. In the FIG. 4 example, the sum-peak appearing at 12.8 keV would be identified as overlapping the characteristic peak of lead, arising from emission of $K_\beta$ x-rays, which appears at 12.6 keV, provided that the window size is set properly.

Returning to FIG. 2, the concentration of the element of interest and the associated LOD is calculated from the energy spectrum data in view of any interfering sum-peak(s), step This calculation involves deconvoluting the contributions of the interfering sum-peak and the characteristic peak to the measured intensity, step 225. As discussed above in connection with the FIG. 3 flowchart, the estimated intensity of the sum-peak may be calculated from the measured intensities of the individual component peaks and the detector time window. The estimated intensity may be subtracted from the measured intensity at the known energy of characteristic radiation of the element of interest to determine the corrected intensity attributable to detection of the characteristic x-rays.

Any suitable procedure may be employed to determine the concentration of the element of interest from the corrected intensity. Various algorithms are well known in the art for calculating the concentration of an element based on measured intensity in the energy spectrum, and include fundamental parameter (FP) methods and methods based on empirical calibrations of the XRF instrument with a collection of standards of known compositions. The appropriate algorithm(s) for calculating elemental concentration will typically be encoded within controller 135 as a set of instructions executable by microprocessor 145. The instruction set may also encode an algorithm for calculating the LOD of the element of interest. Generally described, the LOD for a particular measurement is proportional to the statistical uncertainty of the background counts $N_B$ (including counts attributable to the presence of an interfering sum-peak), divided by the number of counts attributable to the signal $N_S$, as expressed below:

$$LOD \propto \frac{\sqrt{N_B}}{N_S}$$

While increasing the primary x-ray beam current and/or the analysis time will lower the LOD for background counts attributable to certain types of noise, this is not the case for background counts attributable to a sum-peak, and so the LOD cannot be easily reduced by increasing the beam current or analysis time when an interfering sum-peak is present.

Methods for calculation of the LOD (which includes background attributable to the sum-peak and other sources) from the spectral data are well known in the art and need not be discussed herein. It will be recognized that when the background noise comes primarily from the sum-peak, the LOD is substantially independent of the total detected counts of the characteristic peak. The spectra in the region of 12.6 keV, shown in FIG. 5, shows an example in which the sum-peak intensity overwhelms the characteristic line by a factor of about 20 so that the LOD with the sum-peak "background" present is inherently about an order of magnitude greater than the LOD would be if the sum-peak were absent.

In step 230, a criterion is applied to determine if the calculated LOD meets a targeted objective. Such targeted objectives may be set by regulatory requirements. For example, a specific Reduction of Hazardous Substances (RoHS) standard may prescribe an LOD of 100 parts per million (ppm) of lead in a particular matrix or product type. If the result of step 225 meets the targeted objective (e.g., an LOD of 75 ppm is calculated from the acquired spectrum), then the analysis terminates, and the analytical results may be displayed or otherwise output to the operator. If, however, the targeted objective is not satisfied (e.g., an LOD of 200 ppm is calculated), then the method proceeds to step 235. In certain implementations, the criterion used to determine whether the targeted LOD objective is met may be specified by the operator (e.g., by entering an LOD value or selecting a particular regulation to be applied).

In step 235, controller 135 directs filter apparatus 125 to position filter 130 in the emitted beam path. Filter 130 is constructed from a material that preferentially attenuates the x-rays that contribute to the formation of the interfering sum-peak (e.g., the $K_\alpha$ line of iron at 6.4 keV) relative to the characteristic x-rays of the element of interest (e.g., the $K_\beta$ line of lead at 12.6 keV). In one illustrative implementation, filter 130 is fabricated from titanium, which has an absorption cross-section of 357 $cm^2/g$ and 57.5 $cm^2/g$ for 6.4 keV and 12.6 keV x-rays, respectively. A titanium filter having a thickness of 1 mil attenuates the 6.4 keV intensity by a factor of 59 and the associated sum-peak (produced by simultaneous detection of two 6.4 keV x-rays) by a factor of 3500. In contrast, the intensity of the 12.6 keV $K_\beta$ x-rays is attenuated only by a factor of 1.9.

As noted above, filter apparatus 130 may take the form of a filter wheel or similar device having a plurality of filters of differing composition and/or thickness mounted thereon. In this case, controller 135 may be programmed with instructions for selecting a filter from the plurality of candidate filters based on the energy of the x-rays to be preferentially attenuated, and the degree of attenuation required. Controller 135 may then send a signal to filter apparatus 130 to position the selected filter in the emitted radiation path. Controller 135 may also adjust the parameters of the primary x-ray beam (e.g., by increasing the current at x-ray source 105) to compensate for the attenuation of the characteristic x-rays of the element of interest by filter 130, as indicated by step 240.

In steps 245 and 250, the filtered radiation is detected and a filtered energy spectrum is constructed from the processed detector pulses, in much the same manner as described above in connection with steps 210 and 215. Referring again to FIG. 4, the solid line represents an energy spectrum of the iron alloy sample described above, whereby a titanium filter is employed to attenuate the $K_\alpha$ and $K_\beta$ x-rays of iron and consequently suppress the sum-peak at 12.8 keV that obscures the $K_\beta$ peak of lead at 12.6 keV. The x-ray tube current was increased by a factor of 2.5 during acquisition of the filtered energy spectrum to compensate for attenuation of the characteristic x-rays of lead by filter 130. The performance gain effected by filtration of the emitted x-rays may be more easily discerned with reference to FIG. 5, which shows the region of FIG. 4 between 9 keV and 15 keV. In particular, there is little or no evidence in the filtered energy spectrum (solid line) of the large sum-peaks at 12.8 keV and 13.4 keV that appear in the initial (unfiltered) energy spectrum. We note that the 1 mil Ti filter, used for illustration of the principle, was thicker than it needed to be for optimum results. It is further noted that useful sum-peak suppression filters may be constructed from a variety of materials. For example, one can adjust the thicknesses of filters constructed from titanium, vanadium or chromium to achieve equivalent results for suppressing sum-peaks arising from the characteristic x-rays of iron, nickel, copper and/or zinc. The only requirement for selection of the filter material is that its critical absorption energy is lower than the energy(ies) of the x-rays to be suppressed.

Next, the concentration and LOD of the element of interest are calculated from the data in the filtered energy spectrum using the known methods alluded to above, step 255. These results may be displayed or otherwise output to the operator. It will be understood that the suppression of the sum-peak will remove uncertainties arising from the need to subtract the contribution of the sum-peak to the measured intensity of the characteristic peak, and will result in a lower LOD, thereby enabling conformance to more stringent requirements imposed by regulation or a desire for greater sensitivity. In a typical implementation, the additional steps for improving LOD embodied in the present invention require only a small increase in the total analysis cycle time.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of operating an XRF analyzer, comprising:
directing a primary beam of x-ray radiation onto a sample;
detecting radiation emitted from the sample;
constructing an energy spectrum of the detected radiation;
processing the constructed energy spectrum to identify a sum-peak in the energy spectrum that overlaps a characteristic peak of an element of interest, the processing of the constructed energy spectrum including:
calculating a concentration and a limit of detection of the element of interest using information about the identified sum-peak, including deconvoluting the contributions of the interfering sum-peak and the characteristic peak to a measured intensity; and
terminating the analysis when the calculated limit of detection meets a targeted objective;
positioning a filter in the path of the emitted radiation, the filter at least partially inhibiting the passage of radiation of an energy that contributes to the identified sum-peak; and
detecting the filtered radiation, and constructing a filtered spectrum of the detected filtered radiation.

2. The method of claim 1, wherein the step of positioning a filter further comprises adjusting a parameter of the primary x-ray radiation beam to compensate for attenuation of the radiation of the element of interest by the filter.

3. The method of claim 1, wherein the step of positioning the filter comprises selecting a filter from a plurality of available filters based on the energy of the radiation that contributes to the sum-peak.

4. The method of claim 1, wherein the filter is at least partially fabricated of at least one of titanium, vanadium and chromium.

5. The method of claim 1, wherein the element of interest is lead.

6. The method of claim 1, further comprising a step of determining a concentration of the element of interest from the filtered energy spectrum.

7. A method of operating an XRF analyzer, comprising:
directing a primary beam of x-ray radiation onto a sample;
constructing an energy spectrum of the detected radiation:
processing the constructed enemy spectrum to identify a sum-peak in the energy spectrum that overlaps a characteristic peak of an element of interest, the processing of the constructed energy spectrum including:
selecting a characteristic peak in the energy spectrum of an element other than the element of interest;
calculating the intensity products of sum-peaks produced by combination of the selected characteristic peak with each of a set of peaks in the energy spectrum, the set of peaks including the selected peak;
comparing the calculated intensity products to a specified threshold; and
determining whether the energy of each of the sum-peaks that exhibits an intensity that meets the specified threshold is within a window of the characteristic peak of the element of interest;
postioning a filter in the path of the emitted radiation, the filter at least partially inhibiting the passage of radiation of an energy that contributes to the identified sum-peak, and
detecting the filtered radiation, and constructing a filtered spectrum of the detected filtered radiation.

8. The method of claim 7, wherein the step of selecting a characteristic peak includes selecting the characteristic peak having the highest intensity in the energy spectrum.

9. The method of claim 7, wherein the selecting, calculating, comparing and determining steps are repeated for each of a plurality of characteristic peaks of elements other than the element of interest.

10. An x-ray fluorescence (XRF) analyzer, comprising:
an x-ray source for generating a primary x-ray beam to irradiate a sample;
a detector positioned to receive radiation emitted from the sample and configured to responsively produce pulses representative of the energies of the received radiation;
a programmable controller, coupled to the detector, for accumulating and processing the pulses produced by the detector and constructing an energy spectrum of the radiation emitted from the sample;
a filter apparatus for selectively positioning a filter in the path of the emitted radiation;
wherein the programmable controller is programmed with instructions for performing steps of:
constructing an energy spectrum of the detected radiation,
processing the constructed energy spectrum to identify a sum-peak in the energy spectrum that overlaps a characteristic peak of an element of interest, the processing of the constructed energy spectrum including:
calculating a concentration and a limit of detection of the element of interest using information about the identified sum-peak, including, characteristic peak to a measured intensity; and
terminating the analysis when the calculated limit of detection meets a targeted objective;
causing the filter apparatus to position a filter in the path of the emitted radiation that at least partially inhibits the passage of radiation of an energy that contributes to the identified sum-peak; and
constructing a filtered spectrum of the detected filtered radiation.

11. The XRF analyzer of claim 10, wherein the filter apparatus comprises a filter wheel having first and second filters mounted therein, the first and second filters differing in at least one of thickness and material.

12. The XRF analyzer of claim 11, wherein the controller is programmed with instructions for selecting one of the first and second filters based on the energy of the radiation that contributes to the sum-peak.

13. The XRF analyzer of claim 10, wherein the controller is programmed with instructions to adjust a parameter of the primary x-ray beam to compensate for attenuation of fluoresced radiation of the element of interest by the filter.

14. The XRF analyzer of claim 10, wherein the programmable controller is programmed with instructions for calculating a concentration and a limit of detection of the element of interest from the energy spectrum using information about the identified sum-peak and terminating the analysis when the calculated limit of detection meets a targeted objective.

15. The XRF analyzer of claim 10, wherein the programmable controller is programmed with instructions for calculating a concentration of the element of interest based on the filtered energy spectrum.

16. The XRF analyzer of claim 10, wherein the detector is a silicon drift detector.

* * * * *